United States Patent [19]

Brunelle

[11] 4,255,359
[45] Mar. 10, 1981

[54] NON-POLLUTING OXYHYDROCHLORINATION PROCESS

[75] Inventor: Jean-Pierre Brunelle, Fresnes, France

[73] Assignee: Rhone-Poulenc Industries, Paris, France

[21] Appl. No.: 28,380

[22] Filed: Apr. 9, 1979

[30] Foreign Application Priority Data

Apr. 26, 1978 [FR] France .................... 78 12256

[51] Int. Cl.³ .................................. C07C 21/00
[52] U.S. Cl. .................................... 570/243; 423/481
[58] Field of Search ............ 260/654 A, 659 R; 423/481

[56] References Cited

U.S. PATENT DOCUMENTS

| | | | |
|---|---|---|---|
| 2,915,365 | 12/1959 | Saissol | 423/481 |
| 4,049,578 | 9/1977 | Reagan et al. | 252/455 R |
| 4,053,557 | 10/1977 | Kageyama | 423/481 |
| 4,169,862 | 10/1979 | Eden | 260/654 A |

Primary Examiner—Jacqueline V. Howard

[57] ABSTRACT

A non-polluting oxyhydrochlorination process is provided in which the residual gaseous effluents are purified by catalytic oxidation in the presence of a catalyst comprising platinum and/or iridium deposited on a special alumina support of eta crystallographic structure and then washing the effluent before being discharged into the atmosphere.

The process of the invention is particularly applicable to a residual effluent containing essentially carbon monoxide, carbon dioxide, ethylene, 1,2-dichloroethane, and at least one chlorinated hydrocarbon from among the group consisting of chloroform, carbon tetrachloride, ethyl chloride, 1,1-dichloroethane, 1,1,1- and 1,1,]-trichloroethanes, 1,1,2,2- and 1,1,1,2- tetrachloroethanes, vinyl chloride, 1,1- and 1,2-dichloroethylenes, trichloroethylene, perchloroethylene and chloral.

12 Claims, No Drawings

NON-POLLUTING OXYHYDROCHLORINATION PROCESS

BACKGROUND OF THE INVENTION

The present invention relates to a non-polluting oxyhydrochlorination process. More particularly, it relates to a process of oxyhydrochlorination by which the residual gaseous effluents are purified by catalytic oxidation and washing before discharge into the atmosphere.

The conventional methods for producing chlorinated derivatives of ethylene and, in particular, 1,2-dichloroethane, by oxyhydrochlorination do not provide 100 percent selectivity. Thus, the effluent emerging from the oxyhydrochlorination reactor always contains larger or smaller amounts of by-products. These by-products are complex mixtures which contain, in particular, in addition to unreacted hydrochloric acid and ethylene, carbon monoxide, carbon dioxide, and chlorinated organic compounds, such as ethyl chloride, 1,1-dichloroethane, the trichloroethanes, the tetrachloroethanes, the dichloroethylenes, trichloroethylene, chloroform, carbon tetrachloride, chloral, perchlorethylene, etc.

The removal of the chlorinated derivatives of ethylene from the effluent emerging from the oxyhydrochlorination reactor, never having in practice been quantitative, the residual effluent which results therefrom contains nitrogen, oxygen, as well as variable amounts of the chloro derivatives of ethylene which are sought, such as 1,2-dichloroethane, and variable amounts of the by-products mentioned above.

In order to treat such effluents, it has already been proposed, in accordance with French patent application No. 2,279,703, to pass them, at a temperature of between 300° and 450° C., over a catalyst bed, formed of a support of alumina or silica, on which 10 to 50% by weight of chromium oxide has been deposited. However, such a process has the drawback, in particular, that it is not selective and of favoring the Deacon reaction of formation of molecular chlorine from hydrochloric acid and oxygen. This formation of molecular chlorine, differing from hydrochloric acid, is extremely disturbing since it is difficult to eliminate from the gaseous effluents by conventional techniques, such as scrubbing with water. Furthermore, the presence of molecular chlorine in the presence of water vapor may lead to problems of material corrosion which are particularly disturbing at high temperatures. Finally, the catalysts having a base of chromium oxide are of only indifferent effectiveness for the oxidation of carbon monoxide to carbon dioxide.

By means of the present invention a process is provided which makes it possible to obviate these drawbacks and which uses a catalyst which is active, stable, and very selective for the oxidation of the carbon monoxide and hydrocarbons, wether or not chlorinated.

It is, accordingly, an object of the present invention to provide a novel non-polluting process for oxyhydrochlorinating, particularly for oxyhydrochlorinating ethylene, which is free from the disadvantages of the prior art.

It is another object of the invention to provide a non-polluting selective process for the oxidation of carbon monoxide and chlorinated and non-chlorinated hydrocarbons.

It is a further object of the invention to provide catalyst compositions having great utility in treating chlorinated organic compositions containing up to 10 carbon atoms.

Other objects of the invention will be apparent to those skilled in the art from the present description.

GENERAL DESCRIPTION OF THE INVENTION

The present invention concerns a non-polluting oxyhydrochlorination process comprising reacting in a mixture of gaseous hydrogen chloride, air or oxygen, ethylene and/or a chlorinated derivative of ethylene to obtain an effluent containing chlorinated derivatives of ethylene, whereby:

(1) the chlorinated derivatives of ethylene formed during the said oxyhydrochlorination reaction are removed from the effluent, producing a residual effluent containing essentially oxygen, nitrogen, carbon monoxide, carbon dioxide, unreacted ethylene, 1,2-dichloroethane and at least one chlorinated hydrocarbon from the group consisting of chloroform, carbon tetrachloride, ethyl chloride, 1,1-dichloroethane, 1,1,1- and 1,1,2-trichloroethanes, 1,1,2,2- and 1,1,1,2-tetrachloroethanes, vinyl chloride, 1,1- and 1,2-dichloroethylenes, trichloroethylene, perchloroethylene and chloral;

(2) a diluent gas is optionally added to the said residual effluent;

(3) the residual effluent is preheated to a temperature of between about 250° and 400° C.;

(4) this effluent is transferred to an adiabatic reaction zone containing an oxidation catalyst comprising platinum and/or iridium, deposited on a support of alumina of eta crystallographic structure, which, after oxidation, provides a mixture of gases comprising carbon dioxide, hydrochloric acid, water vapor, oxygen and nitrogen;

(5) all or part of the heat liberated upon said oxidation is used to preheat, in accordance with step 3, above, with the use of a heat exchanger, the effluent coming from step 1, above;

(6) the hydrochloric acid formed during the oxidation stage, (4) above, is removed by scrubbing before the effluent is discharged into the atmosphere, or is used as source of inert gas.

The oxyhydrochlorination process in accordance with the invention, therefore, comprises reacting gaseous hydrogen chloride, air or oxygen, ethylene and/or a chlorinated derivative of ethylene to form chlorinated derivatives of ethylene contained in an effluent.

The separation from the effluent of the chlorinated derivatives of ethylene formed during the course of the oxyhydrochlorination reaction consists generally of the following steps: (a) scrubbing the effluent with water to remove the unreacted hydrochloric acid from it, (b) condensation by cooling of the chlorinated derivatives of ethylene, and (c) washing of the effluent with an organic solvent, such as hexachlorobutadiene.

In practice, these different treatments do not make it possible quantitatively to separate the chlorinated derivatives from the gaseous effluent. Thus the residual effluent which results from this separation step contains, in addition to oxygen, nitrogen and unreacted ethylene, chlorinated derivatives of ethylene which have not been removed, such as 1,2-dichloroethane, as well as variable amounts of different by-products, such as carbon monoxide, carbon dioxide, chloroform, carbon tetrachloride, ethyl chloride, 1,1-dichloroethane, 1,1,1- and 1,1,2-trichloroethanes, vinyl chloride, 1,1- and 1,2- dichloroethylenes, trichloroethylene, perchloroethylene, chloral, etc.

If the removal of the chlorinated derivatives of ethylene from the effluent comprises a step of absorption by an organic solvent, such as hexachlorobutadiene, traces of this solvent may also be present in the residual effluent which is to be treated. Generally, the contents by volume of ethylene, carbon dioxide, carbon monoxide and chlorinated organic products in the residual effluent to be treated are on the order of 0.5%, 2%, 1% and 0.5% respectively, the most abundant chlorinated organic product being generally 1,2-dichloroethane. These contents may, however, vary within very wide limits depending on the conditions of use and the nature of the oxyhydrochlorination catalysts employed. The oxygen content of the residual effluent is generally sufficient to permit the oxidation, in a subsequent step, of the products contained therein, that is to say, carbon monoxide, ethylene, and the chlorinated organic products. Otherwise, it is necessary, in accordance with the process of the invention, to add a sufficient amount of air or oxygen to the residual effluent to permit the total oxidation of the aforementioned products.

A diluent gas, such as nitrogen or air, may optionally be added to the residual effluent in order to limit the increase of temperature in the adiabatic reaction zone of the subsequent step. The amount of diluent gas used should be such that the maximum temperature in the reaction zone does not exceed about 600° C., and preferably about 500° C. In fact, above these temperatures, the selectivity of the catalysts in accordance with the process of the present invention decreases due to the formation of molecular chlorine by the Deacon reaction, defined above.

The residual effluent is preheated to a temperature of between about 250° and 400° C., and then transferred to an adiabatic reaction zone containing an oxidation catalyst comprising platinum and/or iridium deposited on a special support of alumina of eta crystallographic structure.

The space velocity of the effluent defined by the ratio of the volumetric flow of the effluent to the volume of catalyst is between about 1000 and 100,000 per hour and preferably between about 5000 and 20,000 per hour.

The oxidation reaction can be carried out at atmospheric pressure. However, in certain cases it may be advantageous to operate at a pressure greater than atmospheric pressure, and, in particular, at a pressure of between about 1 and 10 bars.

The support used for the preparation of the catalysts in accordance with the process of the invention consists of alumina whose crystallographic structure corresponds essentially to the eta form and whose specific surface is between about 200 and 400 m²/g (square meters per gram). This type of alumina is known to those skilled in the art. Some principles concerning its preparation can be found for instance in the technical magazine of the Alcoa Company on alumina oxides and hydroxides entitled, "Technical Paper No. 19," by K. Wefers and G. M. Bell, (1972), page 14, paragraph 2.22, page 40, paragraph 4.12. By way of illustration, the manner of operation thus described can be employed in accordance with the present invention.

An alumina gel cake containing 20% alumina, calculated as $Al_2O_3$, is prepared by dewatering, washing and filtering a suspension of aluminum hydroxide obtained by continuous precipitation of a sodium aluminate solution containing 100 g./l. (grams per liter) of alumina, calculated as $Al_2O_3$, and that the molar ratio $NO_3/Al_2O_3$ is equal to 0.20. The precipitation pH is then approximately at about 8.5. This cake is then again placed in suspension in a 2 N ammoniacal solution of a pH of about 10, so as to obtain a thick suspension of alumina gel containing about 10 to 15% alumina. The paste is maintained under agitation for about 20 hours at 50° C., which makes it possible to obtain a development of more than 50% aluminum hydroxide into bayerite. After drying, shaping and calcining in a dry atmosphere at about 450° C., there is obtained an eta alumina support whose specific surface is on the order of 350 m.²/g. and whose surface acidity is far greater than that of the other crystallographic forms of alumina, namely, chi, gamma, delta, theta, alpha, etc.

The oxidation catalysts which are used in accordance with the process of the invention contain from about 0.02% to 5% by weight platinum and/or iridium, referred to the support. A content of between about 0.1% and 0.5% by weight of platinum and/or iridium is, however, preferred. When both platinum and iridium are employed, the relative proportion by weight of platinum to iridium may vary within wide limits but will preferably be between about 1/10 and 10/1.

The oxidation catalyst in accordance with the process of the invention may be prepared by conventional methods and, in particular, by impregnating the support with solutions of inorganic or organic precursors of platinum and/or iridium. The impregnation can be effected in one or more steps by means of solutions containing metal compounds of platinum and/or iridium.

As soluble compounds of platinum and/or iridium which are conventionally employed mention may be made of chloroplatinic acid, chloroiridic acid, platinum tetramine chloride, etc.

After impregnation of the support with the solution described above, the catalyst is then dried, followed by calcining in a stream of air at a temperature of between about 200° and 800° C. for several hours. The catalyst may advantageously be treated in an atmosphere containing a sulfur derivative, such as hydrogen sulfide. In such case, the reduction or sulfiding reaction can be carried out at any of the steps of the preparation of the catalyst after impregnation of the support, but preferably before the calcining step.

The catalyst may be used in the form of beads, extruded shapes, pellets, or any other shape or form.

As the oxidation reactions are exothermic, there is a liberation of heat in the reaction zone which results in an increase in the temperature of the effluent. All or part of the heat liberated is used to preheat the residual effluent to a temperature of between about 250° and 400° C. by means of a heat exchanger.

The process of the present invention thus makes it possible to oxidize carbon monoxide and chlorinated or non-chlorinated hydrocarbons contained in the residual effluent and to arrive at a gas which is free of molecular chlorine and formed essentially of water vapor, carbon dioxide, hydrochloric acid, oxygen, and nitrogen. The effluent resulting therefrom is then treated, before discharge into the atmosphere or use as source of inert gas, in order to remove the hydrochloric acid from it. This removal is customarily effected in a scrubbing tower, absorbing the hydrochloric acid by an aqueous solution of neutral or alkaline pH.

All or part of the scrubbed effluent can advantageously be recycled to diluent step No. 2, described above, and serve as diluent for the residual effluent before the oxidation step.

The catalyst for the selective oxidation of the chlorinated hydrocarbons in accordance with the process of the invention may be used just as effectively in fields other than the production of chlorinated derivatives of ethylene by oxyhydrochlorination, and, in particular, in fields such as dry cleaning, the scouring of metals, dyeing, and more particularly, in any field employing chlorinated organic products containing 1 to 10 carbon atoms.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified. The examples which follow will serve to explain the invention and, in particular, the importance of the catalysts used in the process of the invention, as compared with the prior art catalyst, as well as the specificity of the nature of the support and of the metals used.

EXAMPLE 1

This example, given by way of comparison, illustrates the importance of the process of the invention as compared with the prior art process using a catalyst having a base of chromium oxide deposited on an alumina support.

There will be described below the preparation of two catalysts in accordance with the process of the invention: (A) 100 g. of extrudates of alumina of eta structure having a specific surface of 300 m.$^2$/g. and a pore volume of 0.55 cc./g. are impregnated with 55 cc. of an aqueous solution of chloroplatinic acid containing 0.20 g. of platinum, or (B) of chloroiridic acid containing 0.20 g. of iridium. After a few hours of contact, the extrudates are dried at 120° C. and then calcined in air at 500° C. for 3 hours.

The catalysts (A) and (B), above, which are obtained, contain 0.2% by weight of platinum and 0.2% by weight of iridium, respectively, deposited on an eta alumina support.

There will now be described the preparation of a catalyst (C) having a base of chromium oxide disclosed in the prior art: 100 g. of extrudates of eta alumina are impregnated with 55 cc. of an aqueous solution of chromic anhydride containing 20 g. of chromium oxide, calculated as $Cr_2O_3$. After a few hours of contact, the extrudates are dried at 120° C., and then calcined in air for 3 hours. The catalyst obtained contains 20% by weight of chromium oxide deposited on an eta alumina support.

The activity and selectivity of the three above catalysts are measured at a space velocity of 5000/hour on a synthetic gas representative of the residual oxyhydrochlorination effluents and consisting of a mixture of, by volume, 1% carbon monoxide, 0.5% 1,2-dichloroethane, 5% oxygen, and 93.5% nitrogen. The conversions of the carbon monoxide measured at 300° C. and of the 1,2-dichloroethane measured at 400° C. are set forth in Table I, below. There are also included in said Table I, the selectivity of the three catalysts for the oxidation of dichloroethane into hydrochloric acid, carbon dioxide and water vapor, as well as any other chlorinated products formed.

TABLE I

|  |  | % conversion of CO at 300° C. | % conversion of 1,2-dichloroethane at 400° C. | % selectivity in HCl at 400° C. | Chlorinated product formed other than HCl |
| --- | --- | --- | --- | --- | --- |
| Invention | CATALYST (A) | 80 | 95 | 100 | none |
|  | CATALYST (B) | 90 | 95 | 100 | none |
| Prior Art | CATALYST (C) | 0 | 75 | 85 | molecular chlorine |

Examination of these results shows very clearly the superiority of the two catalysts (A) and (B), in accordance with the process of the invention, over the prior art catalyst (C) having a base of chromium oxide, more particularly with respect to their oxidizing activity towards carbon monoxide. Furthermore, the selectivity of the two catalysts (A) and (B) in accordance with the process of the invention is equal to 100%, while that of the prior art catalyst (C) is only 85%, with 15% of the dichloroethane in this case being transformed into molecular chlorine by the Deacon reaction.

A 128-hour test carried out under the conditions described above furthermore shows that the catalytic performances of catalysts (A) and (B) of the process of the invention are entirely stable.

EXAMPLE 2

In this example, there is described the preparation of several catalysts having a base of platinum deposited on different supports in order to show the very great superiority and specificity of the support claimed for the preparation of the catalysts by the process of the invention, that is to say, of the support of eta crystallographic alumina structure.

The manner of operation described in Example 1, above, used to prepare catalyst (A) of said example, in accordance with the invention is employed, using the following supports:

(D) balls of alumina of alpha structure whose specific surface is equal to 10 m.$^2$/g. and whose pore volume is equal to 0.50 cc./g.;

(E) balls of activated alumina which were obtained by the process described in U.S. Pat. No. 2,915,365 and have a specific surface of 250 m.$^2$/g. and a pore volume of 0.50 cc./g.;

(F) extrudates of silica-alumina (support having substantial surface acidity) containing 70% silica and having a specific surface of 350 m.$^2$/g. and a pore volume of 0.80 cc./g.;

(G) silica pellets of specific surface 400 m.$^2$/g. having a pore volume of 0.60 cc./g.;

(H) balls of alumina of gamma structure whose specific surface is equal to 200 cm.$^2$/g. and whose pore volume is equal to 0.50 cc./g.;

(I) balls of alumina monohydrite of boehmite structure whose specific surface is equal to 50 m.$^2$/g. and its pore volume to 0.50 cc./g.

After impregnation by a volume equal to the pore volume of the support, of an aqueous solution of chloroplatinic acid containing 0.20 g. of platinum, the catalysts are dried at 120° C. and then calcined at 500° C. in air for 3 hours: the catalysts (D), (E), (F), (G), (H), and (I), respectively, obtained all contain 0.2% by weight of platinum.

The performance of these catalysts measured under the conditions described in Example 1, above, are reported in Table II, below:

TABLE II

|  |  | Nature of the support | % conversion of carbon monoxide at 300° C. | % conversion of 1,2-dichloroethane at 400° C. |
|---|---|---|---|---|
| CATALYST (A) | Invention | eta alumina | 80 | 95 |
| CATALYST (B) | Invention | eta alumina | 90 | 95 |
| CATALYST (D) | Comparative | alpha alumina | 85 | 0 |
| CATALYST (E) | Comparative | activiated alumina | 35 | 55 |
| CATALYST (F) | Comparative | silica alumina | 20 | 30 |
| CATALYST (G) | Comparative | silica | 20 | 10 |
| CATALYST (H) | Comparative | gamma alumina | 70 | 65 |
| CATALYST (I) | Comparative | boehmite | 65 | 35 |

(L) a rhodium trichloride solution containing 0.20 g. of rhodium;

(M) a copper nitrate solution containing 20 g. of cupric oxide.

Catalysts (J), (K), (L), and (M) obtained by this procedure contain 0.2% by weight palladium, 0.2% by weight ruthenium, 0.2% by weight rhodium, and 20% by weight cupric oxide, respectively, deposited on the support of alumina of eta structure described in Example 1, above.

Their oxidizing activity is then measured at a space velocity of 5000 per hour. The gas used consists, as in Example 1, of, by volume, 1% carbon monoxide, 0.5% 1,2-dichloroethane, 5% oxygen, and 93.5% nitrogen. The conversions of the carbon monoxide measured at 300° C. and of the 1,2-dichloroethane measured at 400° C. are contained in Table III, below, ias is the selectivity of the different catalysts for the reaction of oxidation of 1,2-dichloroethane into hydrochloric acid, carbon dioxide, and water vapor.

When the selectivity of the catalysts is not equal to 100%, the nature of the chlorinated products formed, other than the hydrochloric acid, is indicated (molecular chlorine and vinyl chloride).

An examination of the results set forth in Table III, above, very clearly shows the specificity of catalysts

TABLE III

|  |  | Nature of the metal | % conversion of carbon monoxide at 300° C. | % conversion of 1,2-dichloroethane at 400° C. | % selectivity in HCl at 400° C. | Chlorinated product formed other than HCl |
|---|---|---|---|---|---|---|
| Invention | CATALYST (A) | Pt | 80 | 95 | 100 | none |
|  | CATALYST (B) | Ir | 90 | 95 | 100 | none |
| Comparative | CATALYST (J) | Pd | 20 | 85 | 30 | vinyl chloride |
|  | CATALYST (K) | Ru | 15 | 85 | 20 | vinyl chloride |
|  | CATALYST (L) | Rh | 30 | 80 | 50 | vinyl chloride |
|  | CATALYST (M) | Cu | 5 | 20 | 95 | molecular chlorine |

The results set forth in Table II clearly indicate the specificity of the alumina support of eta structure leads to definitely more active catalyst having a base of platinum or iridium by the process of the invention than those using other supports of alumina, silica, or silica alumina. This is particularly clear when one compares conversions of the 1,2-dichloroethane measured at 400° C.

EXAMPLE 3

This example describes below the preparation of various catalysts which differ from the catalysts of the process of the invention, not by the nature of the support, but by the nature of the metal phase.

The manner of operation employed in Example 1 for the preparation of catalysts (A) and (B) of the process of the invention is followed, except that there is no longer used a solution of chloroplatinic acid or of chloroiridic acid, but, instead:

(J) a palladium chloride solution containing 0.20 g. of palladium;

(K) a ruthenium trichloride solution containing 0.20 g. of ruthenium;

(A) and (B) of the process of the invention, containing platinum or iridium, as compared with the catalysts using other precious metals, such as ruthenium, rhodium, or palladium, or non-noble transition metals deemed active in conventional oxidation reactions, such as copper.

The superiority of catalysts (A) and (B) of the invention over catalysts (J), (K), (L), and (M) is particularly evident when one compares their activity measured at 300° C. for the oxidation of carbon monoxide as well as their selectivity measured at 400° C. for the reaction of the oxidation of 1,2-dichloroethane.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

We claim:

1. In a process of non-polluting oxyhydrochlorination in which gaseous hydrogen chloride, air, or oxygen, ethylene and/or a chlorinated derivative of ethylene are reacted to obtain an effluent containing chlorinated derivatives of ethylene, whereby there are removed from said effluent the unwanted chlorinated derivatives of ethylene produced during said oxyhydrochlorination reaction, the residual effluent containing essentially oxygen, nitrogen, carbon monoxide, carbon dioxide, unreacted ethylene, 1,2-dichloroethane and at least one chlorinated hydrocarbon from the group consisting of chloroform, carbon tetrachloride, ethyl chloride, 1,1-dichloroethane, 1,1,1- and 1,1,2-trichloroethanes, 1,1,2,2- and 1,1,1,2-tetrachloroethanes, vinyl chloride, 1,1- and 1,2-dichloroethylenes, trichloroethylene, perchloroethylene and chloral, wherein said residual effluent is preheated to a temperature between about 250° and 400° C.; the improvement comprising subjecting said heated residual effluent to oxidation by the action of an oxidation catalyst comprising the combination of a metal selected from the class consisting of platinum and iridium and mixtures thereof, deposited on a support of alumina of eta crystallographic structure, thereby producing a mixture of gases comprising carbon dioxide, hydrochloric acid, water vapor, oxygen, and nitrogen.

2. A process according to claim 1, wherein a diluent gas is added to said residual effluent prior to said preheating.

3. A process according to claim 1, wherein the chlorinated derivatives of ethylene formed during the oxyhydrochlorination reaction are removed from the effluent by scrubbing with water, condensation, and scrubbing with an organic solvent.

4. A process according to claim 1, wherein a sufficient amount of air or oxygen is added to the residual effluent to permit complete oxidation.

5. A process according to claim 1, wherein the space velocity of said residual effluent is between about 1,000 and 100,000 per hour.

6. A process according to claim 1, wherein said oxidation step is carried out at atmospheric pressure.

7. A process according to claim 1, wherein said oxidation step is carried out at a pressure of between about 1 and 10 bars.

8. A process according to claim 1, wherein the specific surface of the support of alumina of eta crystallographic structure is between about 200 and 400 m.$^2$/g.

9. A process according to claim 1, wherein the oxidation catalyst contains from about 0.02% to 5% by weight of a noble metal selected from the class consisting of platinum and iridium, and mixtures thereof, referred to the support.

10. A process according to claim 2, wherein all or part of the effluent scrubbed is recycled as the said diluent gas.

11. A process of oxyhydrochlorination according to claim 1, wherein at least part of the heat liberated by said oxidation is used to preheat said residual effluent.

12. A process of oxyhydrochlorination according to claim 1, wherein hydrochloric acid formed during said oxidation is removed by scrubbing before the discharge of effluent into the atmosphere or prior to its use as a source of inert gas.

* * * * *

UNITED STATES PATENT AND TRADEMARK OFFICE
CERTIFICATE OF CORRECTION

PATENT NO. : 4,255,359
DATED : March 10, 1981
INVENTOR(S) : Jean-Pierre Brunelle It is certified that error appears in the above—identified patent and that said Letters Patent is hereby corrected as shown below:

Col. 1, line 59, "wether" should be --whether--

Col. 2, line 10, Delete "in"

Col. 3, line 58, "alumina" should be --aluminum--

Col. 8, line 17, "ias" should be --as--

Signed and Sealed this

Fourth Day of August 1981

[SEAL]

Attest:

GERALD J. MOSSINGHOFF

Attesting Officer

Commissioner of Patents and Trademarks